United States Patent [19]

Hitzel et al.

[11] Patent Number: 4,585,775

[45] Date of Patent: Apr. 29, 1986

[54] SUBSTITUTED PYRIDO (1,2-C)IMIDAZO(1,2-A)BENZIMIDAZOLES, PROCESSES FOR THEIR PREPARATION, THEIR USE AND PHARMACEUTICAL PREPARATIONS BASED ON THESE COMPOUNDS

[75] Inventors: Volker Hitzel, Hofheim am Taunus; Gerhard Rackur, Kelkheim; Martin Bickel, Frankfurt am Main, all of Fed. Rep. of Germany

[73] Assignee: Hoechst Aktiengesellschaft, Fed. Rep. of Germany

[21] Appl. No.: 650,106

[22] Filed: Sep. 13, 1984

[30] Foreign Application Priority Data

Sep. 15, 1983 [DE] Fed. Rep. of Germany ....... 3333314

[51] Int. Cl.⁴ ..................... A61K 31/44; C07D 471/12
[52] U.S. Cl. ..................... 514/287; 546/64; 546/278; 546/296
[58] Field of Search ..................... 546/64; 514/287

[56] References Cited

U.S. PATENT DOCUMENTS

| | | | |
|---|---|---|---|
| 3,880,866 | 4/1975 | Herbst et al. | 546/64 |
| 3,880,870 | 4/1975 | Ledig et al. | 546/64 |
| 3,911,130 | 10/1975 | Herbst et al. | 514/287 |
| 4,254,127 | 3/1981 | Vandenberk et al. | 514/318 |
| 4,255,573 | 3/1981 | Adhikary | 546/64 |
| 4,472,409 | 9/1984 | Senn-Bilfinger | 546/271 |

FOREIGN PATENT DOCUMENTS

| | | |
|---|---|---|
| 5129A | 4/1981 | European Pat. Off. . |
| 2211796 | 11/1972 | Fed. Rep. of Germany . |
| 2548340A | 7/1977 | Fed. Rep. of Germany . |
| 3240248A | 6/1983 | Fed. Rep. of Germany . |
| 1525958 | 9/1978 | United Kingdom . |
| 2028317A | 3/1980 | United Kingdom . |

OTHER PUBLICATIONS

Irikura et al., *Chemical Abstracts*, vol. 78, 4251r, 1973.
Brimblecombe et al., *Proceedings of the B.P.S.*, 1/8/75–1/10/75, pp. 435P–436P.

*Primary Examiner*—Donald G. Daus
*Assistant Examiner*—Stephen M. Kapner

[57] ABSTRACT

The invention relates to compounds of the formula

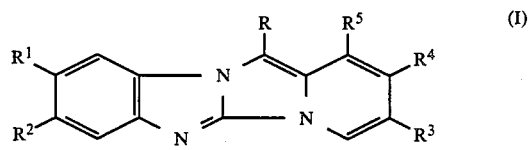

in which $R^1$ and $R^2$ are identical or different and are hydrogen, alkyl, trifluoromethyl, halogen, alkoxycarbonyl, alkoxy or alkanoyl, $R^3$, $R^4$ and $R^5$ are identical or different and are hydrogen, methyl, alkoxy or alkoxyethoxy, and R is hydrogen or a group $SR^6$, in which $R^6$ is the lone, unpaired electron of the 12-sulfenyl radical, hydrogen, optionally substituted alkyl, alkenyl, alkynyl, alkanoyl, optionally mono- or poly-substituted benzoyl, fuoryl, phenacyl, phenoxyacetyl, phenylacetyl or another conventional thiol-protective group, and to physiologically acceptable salts thereof, and to processes for their preparation, to their use as a gastric acid secretion inhibitor and to pharmaceutical preparations based on these compounds.

4 Claims, No Drawings

SUBSTITUTED PYRIDO (1,2-C)IMIDAZO(1,2-A)BENZIMIDAZOLES, PROCESSES FOR THEIR PREPARATION, THEIR USE AND PHARMACEUTICAL PREPARATIONS BASED ON THESE COMPOUNDS

In ulcer therapy, secretion inhibitors, such as $H_2$-antihistamines (for example cimetidine; Brit. J. Pharmacol 53 [1975]435 p) or parasympatholytic agents are also used, in addition to antacids and carbenoxolone. DE-A No. 2,548,340, EP-A No. 5,129 and DE-A No. 3,240,248 have also disclosed substituted 2-benzimidazole 2'-pyridyl sulfoxides which inhibit the exogenically and endogenically stimulated gastric acid secretion and are therefore to be used in pharmaceutical preparations for the treatment of gastro-intestinal lesions, in particular ulcers of the stomach and duodenum.

It has now been found, surprisingly, that the pyrido(1,2-c)imidazo(1,2-a)benzimidazoles, which are accessible, for example, by cyclization or rearrangement of appropriate benzimidazole or benzimidazolone derivatives, are highly effective gastric acid secretion inhibitors.

The invention relates to compounds of the formula

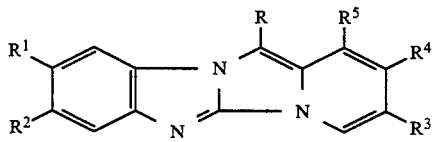

in which $R^1$ and $R^2$ are identical or different and are hydrogen ($C_1$ to $C_6$)-alkyl, trifluoromethyl, halogen, methoxycarbonyl, ethoxycarbonyl, ($C_1$ to $C_5$)-alkoxy or ($C_1$ to $C_4$)-alkanoyl, $R^3$, $R^4$ and $R^5$ are identical or different and are hydrogen, methyl, methoxy, ethoxy, methoxyethoxy or ethoxyethoxy and R is hydrogen or a group $SR^6$, in which $R^6$ is the lone, unpaired electron of a 12-sulfenyl radical, hydrogen, ($C_1$ to $C_6$)-alkyl which can be substituted by ($C_1$ to $C_4$)-alkoxy or mono- or poly-substituted by ($C_6$ to $C_{10}$)-aryl, or is ($C_2$ to $C_6$)-alkenyl, ($C_2$ to $C_6$)-alkynyl, ($C_1$ to $C_7$)-alkanoyl, ($C_5$ to $C_7$)-cycloalkanoyl, benzoyl which can be mono- or poly-substituted by ($C_1$ to $C_7$)-alkyl, ($C_1$ to $C_5$)-alkoxy, ($C_1$ to $C_4$)-alkoxycarbonyl, cyano, trifluoromethyl and-/or halogen, or is furoyl, phenacyl, phenoxyacetyl, phenylacetyl wherein the three latter of which may be substituted as defined for benzoyl or another conventional thiol-protective group, and to physiologically acceptable salts thereof.

Moreover, the invention relates to mixtures of isomers of compounds of the formula I, which are formed, for example, by a rearrangement of compounds, which are unsymmetrically substituted in the benzimidazole moiety, with $R^1 \neq R^2$ of the formula III (see page 17) in the presence of acids.

Protective groups, such as are normally used for protecting thiols, are described, for example, in: Theodora W. Greene, Protective Groups in Organic Synthesis, Wiley-Interscience, New York, 1981, pages 193 et seq.. Those thiol-protective groups are preferred which can be eliminated in the form of physiologically acceptable compounds.

Physiologically acceptable salts of the compounds of the formula I are understood, for example, as water-soluble and water-insoluble acid addition salts, such as the hydrochloride, hydrobromide, hydriodide, phosphate, nitrate, sulfate, acetate, citrate, gluconate, benzoate, butyrate, sulfosalicylate, maleate, laurate, malate, fumarate, succinate, oxalate, tartrate, stearate, methanesulfonate and toluenesulfonate.

On the other hand, base addition salts of compounds of the formula I, in which $R^6$ is hydrogen, can be prepared by reaction with suitable deprotonating agents (for example inorganic or organic bases, such as alkali metal or alkaline earth metal hydroxides or amides, primary, secondary or tertiary aliphatic amines, guanidine or its derivatives).

Alkyl radicals $R^1$ and $R^2$ are suitable alkyl groups having up to 6 carbon atoms, preferably up to 4 carbon atoms, ie. methyl, ethyl, n-propyl, iso-propyl, n-butyl, iso-butyl and tert.-butyl.

Halogen substituents are fluorine, chlorine, bromine and iodine.

Alkoxy radicals $R^1$ and $R^2$ are suitable alkoxy groups having up to 5 carbon atoms, preferably up to 3 carbon atoms, ie. methoxy, ethoxy, n-propoxy or iso-propoxy.

Alkanoyl radicals $R^1$ and $R^2$ preferably have up to 4 carbon atoms and are, for example, formyl, acetyl, propionyl or butyryl, preferably acetyl.

The akyl radical $R^6$ is a suitable alkyl group having up to 6 carbon atoms, preferably up to 4 carbon atoms, ie. methyl, ethyl, n-propyl, iso-propyl, n-butyl, iso-butyl or tert.-butyl. Preferred substituted alkyl groups are methoxymethyl and ethoxymethyl, or benzyl, benzhydryl and triphenylmethyl groups. Alkenyl and alkynyl radicals $R^6$ contain preferably up to 3 carbon atoms, and allyl and propargyl groups may be mentioned as examples. Alkanoyl radicals $R^6$ have preferably up to 7 carbon atoms, and examples are formyl, acetyl, propionyl, butyryl and pivaloyl. Substituted benzoyl radicals $R^6$ are in particular radicals which are mono- or poly-substituted by ($C_1$ to $C_4$)-alkyl, ($C_1$ to $C_4$)-alkoxy, ($C_1$ to $C_4$)-alkoxycarbonyl or halogen radicals, or radicals substituted by cyano or trifluoromethyl. Cycloalkanoyl is preferably cyclohexylcarbonyl.

The following may be mentioned as compounds according to the invention, however without restricting the invention thereto:

Pyrido(1,2-c)imidazo(1,2-a)benzimidazole-12-sulfenyl,
12-Mercapto-pyrido(1,2-c)imidazo(1,2-a)benzimidazole,
12-Methylthio-pyrido(1,2-c)imidazo(1,2-a)benzimidazole,
12-Ethylthio-pyrido(1,2-c)imidazo(1,2-a)benzimidazole,
12-n-Propylthio-pyrido(1,2-c)imidazo(1,2-a)benzimidazole,
12-tert.-Butylthio-pyrido(1,2-c)imidazo(1,2-a)benzimidazole,
12-Methoxymethylthio-pyrido(1,2-c)imidazo(1,2-a)benzimidazole,
12-Ethoxymethylthio-pyrido(1,2-c)imidazo(1,2-a)benzimidazole,
12-Benzylthio-pyrido(1,2-c)imidazo(1,2-a)benzimidazole,
12-Benzhydrylthio-pyrido(1,2-c)imidazo(1,2-a)benzimidazole,
12-Tritylthio-pyrido(1,2-c)imidazo(1,2-a)benzimidazole,
12-Formylthio-pyrido(1,2-c)imidazo(1,2-a)benzimidazole,
Acetylthio-pyrido(1,2-c)imidazo(1,2-a)benzimidazole, 12-Propionylthio-pyrido(1,2-c)imidazo(1,2-a)benzimidazole,
12-Butyrylthio-pyrido(1,2-c)imidazo(1,2-a)benzimidazole,
12-Pivaloylthio-pyrido(1,2-c)imidazo(1,2-a)benzimidazole,
12-Benzoylthio-pyrido(1,2-c)imidazo(1,2-a)benzimidazole,
pyrido(1,2-c)imidazo(1,2-a)benzimidazole,
12-(3-Methoxybenzoyl)thio-pyrido(1,2-c)imidazo(1,2-a)benzimidazole,
12-(3-Chlorobenzoyl)thio-pyrido(1,2-c)imidazo(1,2-a)benzimidazole,
12-Phenylacetylthio-pyrido(1,2-c)imidazo(1,2-a)benzimidazole,
8-Methyl-pyrido(1,2-c)imidazo(1,2-a)benzimidazole-12-sulfenyl,
9-Methyl-pyrido(1,2-c)imidazo(1,2-a)benzimidazole-12-sulfenyl,
8-tert.-Butyl-pyrido(1,2-c)imidazo(1,2-a)benzimidazole-12-sulfenyl,
9-tert.-Butyl-pyrido(1,2-c)imidazo(1,2-a)benzimidazole-12-sulfenyl,
3-Ethyl-pyrido(1,2-c)imidazo(1,2-a)benzimidazole-12-sulfenyl,
2-Methyl-pyrido(1,2-c)imidazo(1,2-a)benzimidazole-12-sulfenyl,
2-Methoxy-pyrido(1,2-c)imidazo(1,2-a)benzimidazole-12-sulfenyl,
8-Ethoxycarbonyl-pyrido(1,2-c)imidazo(1,2-a)benzimidazole-12-sulfenyl,
9-Ethoxycarbonyl-2-methoxy-pyrido(1,2-c)imidazo(1,2-a)benzimidazole-12-sulfenyl,
9-Ethoxycarbonyl-2-methoxy-pyrido(1,2-c)imidazo(1,2-a)benzimidazole-12-sulfenyl,
12-Acetylthio-8-methyl-pyrido(1,2-c)imidazo(1,2-a)benzimidazole,
12-Acetylthio-9-methyl-pyrido(1,2-c)imidazo(1,2-a)benzimidazole,
12-Acetylthio-8-tert.-butyl-pyrido(1,2-c)imidazo(1,2-a)benzimidazole,
12-Acetylthio-9-tert.-butyl-pyrido(1,2-c)imidazo(1,2-a)benzimidazole,
12-Acetylthio-3-ethyl-pyrido(1,2-c)imidazo(1,2-a)benzimidazole,
12-Acetylthio-2-methyl-pyrido(1,2-c)imidazo(1,2-a)benzimidazole,
12-Acetylthio-2-methoxy-pyrido(1,2-c)imidazo(1,2-a)benzimidazole,
12-Acetylthio-8-ethoxycarbonyl-pyrido(1,2-c)imidazo(1,2-a)benzimidazole,
12-Acetylthio-9-ethoxycarbonyl-pyrido(1,2-c)imidazo(1,2-a)benzimidazole,
12-Acetylthio-8-ethoxycarbonyl-2-methoxy-pyrido(1,2-c)imidazo(1,2-a)benzimidazole,
12-Acetylthio-9-ethoxycarbonyl-2-methoxy-pyrido(1,2-c)imidazo(1,2-a)benzimidazole,
2,8-Dimethoxy-1,3-dimethyl-pyrido(1,2-c)imidazo(1,2-a)benzimidazole-12-sulfenyl
2,8-Dimethoxy-1,3-dimethyl-12-mercapto-pyrido(1,2-c)imidazo(1,2-a)benzimidazole,
2,8-Dimethoxy-1,3-dimethyl-12-methylthio-pyrido(1,2-c)imidazo(1,2-a)benzimidazole,
2,8-Dimethoxy-1,3-dimethyl-12-methylthio-pyrido(1,2-c)imidazo(1,2-a)benzimidazole,
2,8-Dimethoxy-1,3-dimethyl-12-ethylthio-pyrido(1,2-c)imidazo(1,2-a)benzimidazole,
2,8-Dimethoxy-1,3-dimethyl-12-n-propylthio-pyrido(1,2-c)imidazo(1,2-a)benzimidazole,
2,8-Dimethoxy-1,3-dimethyl-12-tert.-butylthio-pyrido(1,2-c)imidazo(1,2-a)benzimidazole,
2,8-Dimethoxy-1,3-dimethyl-12-methoxymethylthio-pyrido(1,2-c)imidazo(1,2-a)benzimidazole,
2,8-Dimethoxy-1,3-dimethyl-12-ethoxymethylthio-pyrido(1,2-c)imidazo(1,2-a)benzimidazole,
2,8-Dimethoxy-1,3-dimethyl-12-benzylthio pyrido(1,2-c)imidazo(1,2-a)benzimidazole,
2,8-Dimethoxy-1,3-dimethyl-12-benzhydrylthio-pyrido(1,2-c)imidazo(1,2-a)benzimidazole,
2,8-Dimethoxy-1,3-dimethyl-12-tritylthio-pyrido(1,2-c)imidazo(1,2-a)benzimidazole,
2,8-Dimethoxy-1,3-dimethyl-12-formylthio-pyrido(1,2-c)imidazo(1,2-a)benzimidazole,
2,8-Dimethoxy-1,3-dimethyl-12-acetylthio-pyrido(1,2-c)imidazo(1,2-a)benzimidazole,
2,8-Dimethoxy-1,3-dimethyl-12-propionylthio-pyrido(1,2-c)imidazo(1,2-a)benzimidazole,
2,8-Dimethoxy-1,3-dimethyl-12-butyrylthio-pyrido(1,2-c)imidazo(1,2-a)benzimidazole,
2,8-Dimethoxy-1,3-dimethyl-12-pivaloylthio-pyrido(1,2-c)imidazo(1,2-a)benzimidazole,
2,8-Dimethoxy-1,3-dimethyl-12-benzoylthio-pyrido(1,2-c)imidazo(1,2-a)benzimidazole,
2,8-Dimethoxy-1,3-dimethyl-12-(3-methoxybenzoyl)thio-pyrido(1,2-c)imidazo(1,2-a)benzimidazole,
2,8-Dimethoxy-1,3-dimethyl-12-(3-chlorobenzoyl)thio-pyrido(1,2-c)imidazo(1,2-a)benzimidazole,
2,8-Dimethoxy-1,3-dimethyl-12-phenylacetylthio-pyrido(1,2-c)imidazo(1,2-a)benzimidazole,
2,9-Dimethoxy-1,3-dimethyl-pyrido(1,2-c)imidazo(1,2-a)benzimidazole-12-sulfenyl, 12-mercapto-2,9-Dimethoxy-1,3dimethyl pyrido(1,2-c)imidazo(1,2-a)benzimidazole,
2,9-Dimethoxy-1,3-dimethyl-12-methylthio-pyrido(1,2-c)imidazo(1,2-a)benzimidazole,
2,9-Dimethoxy-1,3-dimethyl-12-ethylthio-pyrido(1,2-c)imidazo(1,2-a)benzimidazole,
2,9-Dimethoxy-1,3-dimethyl-12-n-propylthio-pyrido(1,2-c)imidazo(1,2-a)benzimidazole,
2,9-Dimethoxy-1,3-dimethyl-12-tert.-butylthio-pyrido(1,2-c)imidazo(1,2-a)benzimidazole,
2,9-Dimethoxy-1,3-dimethyl-12-methoxymethylthio-pyrido(1,2-c)imidazo(1,2-a)benzimidazole,
2,9-Dimethoxy-1,3-dimethyl-12-ethoxymethylthio-pyrido(1,2-c)imidazo(1,2-a)benzimidazole,
2,9-Dimethoxy-1,3-dimethyl-12-benzylthio-pyrido(1,2-c)imidazo(1,2-a)benzimidazole,
2,9-Dimethoxy-1,3-dimethyl-12-benzhydrylthio-pyrido(1,2-c)imidazo(1,2-a)benzimidazole,
2,9-Dimethoxy-1,3-dimethyl-12-tritylthio-pyrido(1,2-c)imidazo(1,2-a)benzimidazole,
2,9-Dimethoxy-1,3-dimethyl-12-formylthio-pyrido(1,2-c)imidazo(1,2-a)benzimidazole,
2,9-Dimethoxy-1,3-dimethyl-12-acetylthio-pyrido(1,2-c)imidazo(1,2-a)benzimidazole,
2,9-Dimethoxy-1,3-dimethyl-12-propionylthio-pyrido(1,2-c)imidazo(1,2-a)benzimidazole,
2,9-Dimethoxy-1,3-dimethyl-12-butyrylthio-pyrido(1,2-c)imidazo(1,2-a)benzimidazole,
2,9-Dimethoxy-1,3-dimethyl-12-pivaloylthio-pyrido(1,2-c)imidazo(1,2-a)benzimidazole,
2,9-Dimethoxy-1,3-dimethyl-12-benzoylthio-pyrido(1,2-c)imidazo(1,2-a)benzimidazole,
2,9-Dimethoxy-1,3-dimethyl-12-(3-methoxybenzoyl)thio-pyrido(1,2-c)imidazo(1,2-a)benzimidazole, 2,9-Dimethoxy-1,3-dimethyl-12-(3-chlorobenzoyl)thio-pyrido(1,2-c)imidazo(1,2-a)benzimidazole,
2,9-Dimethoxy-1,3-dimethyl-12-(3-chlorobenzoyl)thio-pyrido(1,2-c)imidazo(1,2-a)benzimidazole,
2,9-Dimethoxy-1,3-dimethyl-12-phenylacetylthio-pyrido(1,2-c)imidazo(1,2-a)benzimidazole,
2,9-Dimethoxy-1,3-dimethyl-pyrido(1,2-c)imidazo(1,2-a)benzimidazole,
2-Methoxy-1,3-dimethyl-8-trifluormethyl-pyrido(1,2-c)imidazo(1,2-a)benzimidazole-12-sulfenyl,
2-Methoxy-1,3-dimethyl-8-trifluoromethyl-12-mercapto-pyrido(1,2-c)imidazo(1,2-a)benzimidazole,
2-Methoxy-1,3-dimethyl-8-trifluoromethyl-12-methylthio-pyrido(1,2-c)imidazo(1,2-a)benzimidazole,
2-Methoxy-1,3-dimethyl-8-trifluoromethyl-12-ethylthio-pyrido(1,2-c)imidazo(1,2-a)benzimidazole,
2-Methoxy-1,3-dimethyl-8-trifluoromethyl-12-n-propylthio-pyrido(1,2-c)imidazo(1,2-a)benzimidazole,
2-Methoxy-1,3-dimethyl-8-trifluoromethyl-12-tert.-butylthio-pyrido(1,2-c)imidazo(1,2-a)benzimidazole,
2-Methoxy-1,3-dimethyl-8-trifluoromethyl-12-methoxymethylthio-pyrido(1,2-c)imidazo(1,2-a)benzimidazole,
2-Methoxy-1,3-dimethyl-8-trifluoromethyl-12-ethoxymethylthio-pyrido(1,2-c)imidazo(1,2-a)benzimidazole,
2-Methoxy-1,3-dimethyl-8-trifluoromethyl-12-benzylthio-pyrido(1,2-c)imidazo(1,2-a)benzimidazole,
2-Methoxy-1,3-dimethyl-8-trifluoromethyl-12-tert.-butylthio-pyrido(1,2-c)imidazo(1,2-a)benzimidazole,
2-Methoxy-1,3-dimethyl-8-trifluoromethyl-12-methoxymethylthio-pyrido(1,2-c)imidazo(1,2-a)benzimidazole,
2-Methoxy-1,3-dimethyl-8-trifluoromethyl-12-ethoxymethylthio-pyrido(1,2-c)imidazo(1,2-a)benzimidazole,
2-Methoxy-1,3-dimethyl-8-trifluoromethyl-12-benzylthio-pyrido(1,2-c)imidazo(1,2-a)benzimidazole,
2-Methoxy-1,3-dimethyl-8-trifluoromethyl-12-benzhydrylthio-pyrido(1,2-c)imidazo(1,2-a)benzimidazole,
2-Methoxy-1,3-dimethyl-8-trifluoromethyl-12-tritylthio-pyrido(1,2-c)imidazo(1,2-a)benzimidazole,
2-Methoxy-1,3-dimethyl-8-trifluoromethyl-12-formylthio-pyrido(1,2-c)imidazo(1,2-a)benzimidazole,
2-Methoxy-1,3-dimethyl-8-trifluoromethyl-12-acetylthio-pyrido(1,2-c)imidazo(1,2-a)benzimidazole,
2-Methoxy-1,3-dimethyl-8-trifluoromethyl-12-propionylthio-pyrido(1,2-c)imidazo(1,2-a)benzimidazole,
2-Methoxy-1,3-dimethyl-8-trifluoromethyl-12-butyrylthio pyrido(1,2-c)imidazo(1,2-a)benzimidazole,
2-Methoxy-1,3-dimethyl-8-trifluoromethyl-12-pivaloylthio-pyrido(1,2-c)imidazo(1,2-a)benzimidazole,
2-Methoxy-1,3-dimethyl-8-trifluoromethyl-12-benzoylthio-pyrido(1,2-c)imidazo(1,2-a)benzimidazole,
2-Methoxy-1,3-dimethyl-8-trifluoromethyl-12-(3-methoxybenzoyl)thio-pyrido(1,2-c)imidazo(1,2-a)benzimidazole,
2-Methoxy-1,3-dimethyl-8-trifluoromethyl-12-(3-chlorobenzoyl)thio-pyrido(1,2-c)imidazo(1,2-a)benzimidazole,
2-Methoxy-1,3-dimethyl-8-trifluoromethyl-12-phenylacetylthio-pyrido(1,2-c)imidazo(1,2-a)benzimidazole,
2-Methoxy-1,3-dimethyl-9-trifluoromethyl-pyrido(1,2-c)imidazo(1,2-a)benzimidazole-12-sulfenyl,
2-Methoxy-1,3-dimethyl-8-trifluoromethyl-12-mercapto-pyrido(1,2-c)imidazo(1,2-a)benzimidazole,
2-Methoxy-1,3-dimethyl-8-trifluoromethyl-12-Methylthio-pyrido(1,2-c)imidazo(1,2-a)benzimidazole,
2-Methoxy-1,3-dimethyl-9-trifluoromethyl-12-ethylthio-pyrido(1,2-c)imidazo(1,2-a)benzimidazole,
2-Methoxy-1,3-dimethyl-9-trifluoromethyl-12-n-propylthio-pyrido(1,2-c)imidazo(1,2-a)benzimidazole,
2-Methoxy-1,3-dimethyl-9-trifluoromethyl-12-tert.-butylthio-pyrido(1,2-c)imidazo(1,2-a)benzimidazole,
2-Methoxy-1,3-dimethyl-9-trifluoromethyl-12-methoxymethylthio-pyrido(1,2-c)imidazo(1,2-a)benzimidazole,
2-Methoxy-1,3-dimethyl-9-trifluoromethyl-12-ethoxymethylthio-pyrido(1,2-c)imidazo(1,2-a)benzimidazole,
2-Methoxy-1,3-dimethyl-9-trifluoromethyl-12-benzylthio-pyrido(1,2-c)imidazo(1,2-a)benzimidazole,
2-Methoxy-1,3-dimethyl-9-trifluoromethyl-12-benzhydrylthio-pyrido(1,2-c)imidazo(1,2-a)benzimidazole,
2-Methoxy-1,3-dimethyl-9-trifluoromethyl-12-tritylthio-pyrido(1,2-c)imidazo(1,2-a)benzimidazole,
2-Methoxy-1,3-dimethyl-9-trifluoromethyl-12-formylthio-pyrido(1,2-c)imidazo(1,2-a)benzimidazole,
2-Methoxy-1,3-dimethyl-9-trifluoromethyl-12-acetylthio-pyrido(1,2-c)imidazo(1,2-a)benzimidazole,
2-Methoxy-1,3-dimethyl-9-trifluoromethyl-12-propionylthio-pyrido(1,2-c)imidazo(1,2-a)benzimidazole,
2-Methoxy-1,3-dimethyl-9-trifluoromethyl-12-butyrylthio-pyrido(1,2-c)imidazo(1,2-a)benzimidazole,
2-Methoxy-1,3-dimethyl-9-trifluoromethyl-12-pivaloylthio-pyrido(1,2-c)imidazo(1,2-a)benzimidazole,
2-Methoxy-1,3-dimethyl-9-trifluoromethyl-12-benzoylthio-pyrido(1,2-c)imidazo(1,2-a)benzimidazole,
2-Methoxy-1,3-dimethyl-9-trifluoromethyl-12-(3-methoxybenzoyl)thio-pyrido(1,2-c)imidazo(1,2-a)benzimidazole,
2-Methoxy-1,3-dimethyl-9-trifluoromethyl-12-(3-chlorobenzoyl)thio-pyrido(1,2-c)imidazo(1,2-a)benzimidazole,
2-Methoxy-1,3-dimethyl-9-trifluoromethyl-12-phenylacetylthio-pyrido(1,2-c)imidazo(1,2-a)benzimidazole,
2-Methoxy-1,3-dimethyl-9-trifluoromethyl-pyrido(1,2-c)imidazo(1,2-a)benzimidazole,
8-Methoxycarbonyl-1,9-dimethyl-pyrido(1,2-c)imidazo(1,2-a)benzimidazole-12-sulfenyl,
8-Methoxycarbonyl-1,9-dimethyl-12-Mercapto-pyrido(1,2-c)imidazo(1,2-a)benzimidazole,
8-Methoxycarbonyl-1,9-dimethyl-12-Methylthio-pyrido(1,2-c)imidazo(1,2-a)benzimidazole,
8-Methoxycarbonyl-1,9-dimethyl-12-Ethylthio-pyrido(1,2-c)imidazo(1,2-a)benzimidazole,
8-Methoxycarbonyl-1,9-dimethyl-12-n-Propylthio-pyrido(1,2-c)imidazo(1,2-a)benzimidazole,
8-Methoxycarbonyl-1,9-dimethyl-12-tert.-butylthio-pyrido(1,2-c)imidazo(1,2-a)benzimidazole,
8-Methoxycarbonyl-1,9-dimethyl-12-methoxymethylthio-pyrido(1,2-c)imidazo(1,2-a)benzimidazole,
8-Methoxycarbonyl-1,9-dimethyl-12-ethoxymethylthio-pyrido(1,2-c)imidazo(1,2-a)benzimidazole,
8-Methoxycarbonyl-1,9-dimethyl-12-benzylthio-pyrido(1,2-c)imidazo(1,2-a)benzimidazole,
8-Methoxycarbonyl-1,9-dimethyl-12-benzhydrylthio-pyrido(1,2-c)imidazo(1,2-a)benzimidazole,
8-Methoxycarbonyl-1,9-dimethyl-12-tritylthio-pyrido(1,2-c)imidazo(1,2-a)benzimidazole,
8-Methoxycarbonyl-1,9-dimethyl-12-formylthio-pyrido(1,2-c)imidazo(1,2-a)benzimidazole,
8-Methoxycarbonyl-1,9-dimethyl-12-acetylthio-pyrido(1,2-c)imidazo(1,2-a)benzimidazole,
8-Methoxycarbonyl-1,9-dimethyl-12-propionylthio-pyrido(1,2-c)imidazo(1,2-a)benzimidazole, 8-Methoxycarbonyl-1,9-dimethyl-12-butyrylthio-pyrido(1,2-c)imidazo(1,2-a)benzimidazole,
8-Methoxycarbonyl-1,9-dimethyl-12-pivaloylthio-pyrido(1,2-c)imidazo(1,2-a)benzimidazole,
8-Methoxycarbonyl-1,9-dimethyl-12-benzoylthio-pyrido(1,2-c)imidazo(1,2-a)benzimidazole,
8-Methoxycarbonyl-1,9-dimethyl-12-(3-methoxybenzoyl)thio-pyrido(1,2-c)imidazo(1,2-a)benzimidazole,
8-Methoxycarbonyl-1,9-dimethyl-12-(3-chlorobenzoyl)thio-pyrido(1,2-c)imidazo(1,2-a)benzimidazole,
8-Methoxycarbonyl-1,9-dimethyl-12-phenylacetylthio-pyrido(1,2-c)imidazo(1,2-a)benzimidazole,
8-Methoxycarbonyl-1,9-dimethyl-pyrido(1,2-c)imidazo(1,2-a)benzimidazole,
9-Methoxycarbonyl-1,8-dimethyl-pyrido(1,2-c)imidazo(1,2-a)benzimidazole-12-sulfenyl,
9-Methoxycarbonyl-1,8-dimethyl-12-mercapto-pyrido(1,2-c)imidazo(1,2-a)benzimidazole,
9-Methoxycarbonyl-1,8-dimethyl-12-methylthio-pyrido(1,2-c)imidazo(1,2-a)benzimidazole,
9-Methoxycarbonyl-1,8-dimethyl-12-ethylthio-pyrido(1,2-c)imidazo(1,2-a)benzimidazole,
9-Methoxycarbonyl-1,8-dimethyl-12-n-propylthio-pyrido(1,2-c)imidazo(1,2-a)benzimidazole,
9-Methoxycarbonyl-1,8-dimethyl-12-tert.-butylthio-pyrido(1,2-c)imidazo(1,2-a)benzimidazole,
9-Methoxycarbonyl-1,8-dimethyl-12-methoxymethylthio-pyrido(1,2-c)imidazo(1,2-a)benzimidazole,
9-Methoxycarbonyl-1,8-dimethyl-12-ethoxymethylthio-pyrido(1,2-c)imidazo(1,2-a)benzimidazole,
9-Methoxycarbonyl-1,8-dimethyl-12-benzylthio-pyrido(1,2-c)imidazo(1,2-a)benzimidazole,
9-Methoxycarbonyl-1,8-dimethyl-12-benzhydrylthio-pyrido(1,2-c)imidazo(1,2-a)benzimidazole,
9-Methoxycarbonyl-1,8-dimethyl-12-tritylthio-pyrido(1,2-c)imidazo(1,2-a)benzimidazole,
9-Methoxycarbonyl-1,8-dimethyl-12-formylthio-pyrido(1,2-c)imidazo(1,2-a)benzimidazole,
9-Methoxycarbonyl-1,8-dimethyl-12-acetylthio-pyrido(1,2-c)imidazo(1,2-a)benzimidazole,
9-Methoxycarbonyl-1,8-dimethyl-12-propionylthio-pyrido(1,2-c)imidazo(1,12-a)benzimidazole,
9-Methoxycarbonyl-1,8-dimethyl-12-butyrylthio-pyrido(1,2-c)imidazo(1,2-a)benzimidazole,
9-Methoxycarbonyl-1,8-dimethyl-12-pivaloylthio-pyrido(1,2-c)imidazo(1,2-a)benzimidazole,
9-Methoxycarbonyl-1,8-dimethyl-12-(3-chlorobenzoyl)thio-pyrido(1,2-c)imidazo(1,2-a)benzimidazole,
9-Methoxycarbonyl-1,8-dimethyl-12-phenylacetylthio-pyrido(1,2-c)imidazo(1,2-a)benzimidazole.

The invention also relates to a process for the preparation of compounds of the formula (I), which comprises, (a₁) for the preparation of compounds of the formula I with R=hydrogen, cyclizing compounds of the formula II,

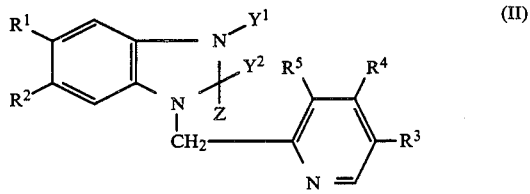

in which $R^1$ to $R^5$ are as defined above and either $Y^1+Y^2$ together represent a bond and Z is a leaving group, such as halogen, preferably chlorine, or $Y^1$ is hydrogen and $Y^2+Z$ together are an oxo group, or (a₂) cyclizing compounds of the formula IIIa

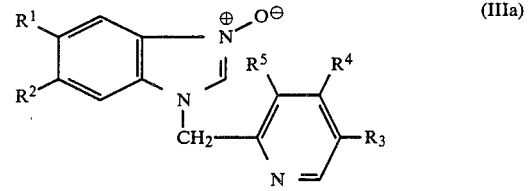

in which $R^1$ to $R^5$ are as defined above, preferably using trifluoroacetic anhydride, toluenesulfonyl chloride, methanesulfonyl chloride and the like, and (b) for the preparation of compounds of the formula I with R=sulfenyl, (b₁) treating 2-benzimidazole 2'-pyridyl sulfoxides of the formula III

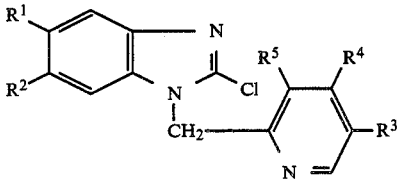

in which $R^1$ to $R^5$ are as defined above, with an acid, in which case mixtures of positionally isomeric compounds are formed if $R^1 \neq R^2$, or (b₂) reacting compounds of the formula I, in which $R^1$ to $R^5$ are as defined above and R is hydrogen, with elemental sulfur or with $S_2Cl_2$ in a solvent, or, (c) for the preparation of compounds of the formula I with R=hydrogen or sulfenyl, reducing compounds of the formula I, in which $R^1$ to $R^5$ are as defined above and R is sulfenyl, to compounds of the formula I, in which $R^6$ is hydrogen, and, if desired, reacting the latter compounds with compounds of the formula $R^6X$, in which $R^6$ is as defined above with the exception of a free-radical electron and hydrogen and X is a leaving group, and, if desired, converting the compounds obtained according to (a₁)–(c) into their physiologically acceptable salts.

In process variant (a₁), preferably a benzimidazole derivative of the formula VII

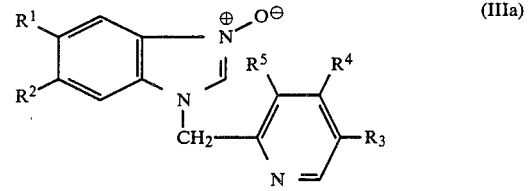

(VII)

in which $R^1$ to $R^5$ are as defined above, is cyclized under suitable conditions, such as, for example, by heating in an organic solvent in the presence of a strong acid (for example in ethanolic hydrochloric acid) to a temperature below the boiling point; or a benzimidazolone derivative of the formula VIII

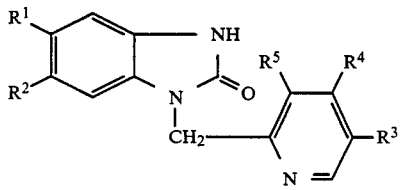

(VIII)

in which $R^1$ to $R^5$ are as defined above, is cyclized under suitable conditions, such as, for example, with acid or a halide thereof (such as polyphosphoric acid or phosphorus oxychloride), preferably by boiling with phosphorus oxychloride under reflux; or a benzimidazole-N-oxide derivative of the formula IIIa

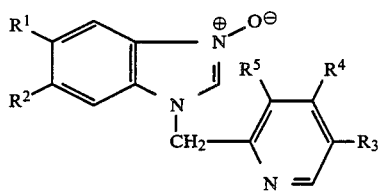

(IIIa)

in which $R^1$–$R^5$ are as defined above, is cyclized under suitable conditions, for example in inert solvents, such as $CH_2Cl_2$, $CHCl_3$, $CCl_4$, ether or THF, by means of trifluoroacetic anhydride, TsCl, MesCl between 0°–100° C., preferably at room temperature.

In process variant (b₁), the rearrangement is carried out preferably in solvents, in particular in aqueous solution in the presence of inorganic or organic acids, such as, for example, HCl, $H_2SO_4$, $HClO_4$, $CF_3COOH$ or similar suitable acids or mixtures thereof, preferably at pH values of about pH 1 at temperatures between 0° and 60° C.

The starting compounds of the formula III and processes for their preparation are, inter alia, known from the abovementioned Offenlegungsschriften DE-A No. 2,548,340, EP-A No. 5,129 and DE-A No. 3,240,248.

The reaction of compounds of the formula I with R=hydrogen, according to process variant (b₂) with elemental sulfur is preferably carried out without a solvent at temperatures above the melting point of sulfur, whereas the reaction with $S_2Cl_2$ is carried out in an inert organic solvent, such as diethyl ether, THF, methylene chloride or chloroform or mixtures thereof, preferably between 0° C. and room temperature.

The process according to (c) has the feature that the reduction of the compound of the formula I with R=sulfenyl is carried out in organic solvents, preferably in ethers, such as diethyl ether or THF, to which advantageously a little water or alcohol is added, with complex hydrides or other suitable reducing agents, at temperatures between 0° and 60° C., preferably at room temperature. Because the resulting thiol compound can readily be oxidized, this is advantageously done under an inert gas blanket. If appropriate, the alkylating or acylating agent R₆X is added immediately after the end of the reduction, in which case it may be necessary to cool the reaction solution. Those skilled in the art are, from their specialist knowledge, familiar with suitable leaving groups X. Such alkylating agents can be, for example, halogens or tosylates, and acylating agents can also be halogens, or carboxylates or toluene sulfonates.

The product can be isolated and purified by column chromatography or crystallization.

The invention also relates to compounds of the formula II, in which $R^1$ to $R^5$, $Y^1$, $Y^2$ and Z are as defined above, and to a process for their preparation, which comprises, (a) for the preparation of a compound of the formula II with $Y^1$ and $Y^2$=a bond and Z=a leaving group, preferably halogen, such as chlorine, reacting a compound of the formula IV

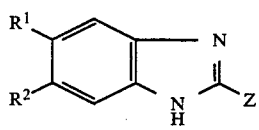

(IV)

in which $R^1$, $R^2$ and Z are as defined above, with an optionally substituted picolyl halide of the formula V

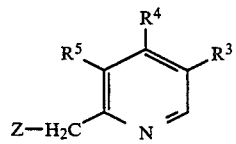

(V)

in which $R^3$ to $R^5$ and Z are as defined above, or (b) for the preparation of a compound of the formula II with $Y^1$=hydrogen and $Y^2$+Z=oxo, reacting a compound of the formula VI

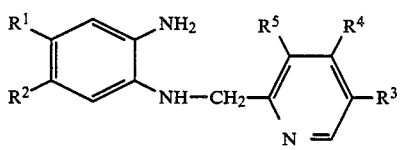

(VI)

in which $R^1$ to $R^5$ are as defined above, with a carbonic acid derivative, such as urea.

The starting compounds of the formulae IV and V are known from the literature or are prepared by known analogy processes.

For example, substituted o-phenylenediamines of the formula VI are prepared by reacting a suitably substituted o-nitroaniline with a suitably substituted 2-pyridinealdehyde to give the Schiff base of the formula IX

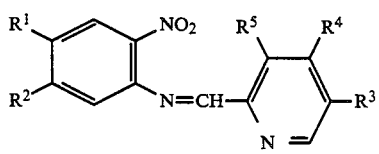

(IX)

$R^1$ to $R^5$ being as defined above, and then reducing the product to the substituted o-nitroamine of the formula X

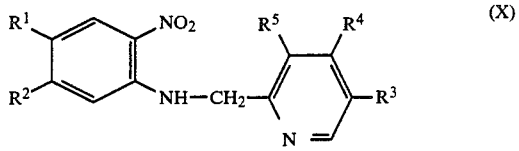

and hydrogenating the latter to the substituted o-phenylenediamine of the formula VI.

The reduction of the compounds of the formula IX is advantageously carried out with NaBH$_4$ or another suitable hydride, preferably under reflux in ethanol. The nitro group of the compounds of the formula X is reduced by means of suitable reducing agents, such as H$_2$/Raney nickel, SnCl$_2$/HCl or Zn/HCl (in this connection, cf. Houben-Weyl, Methoden der organischen Chemie [Methods of organic chemistry], Thieme-Verlag Stuttgart 1957, 4th edition, volume 11/1, pages 360 et seq.).

The starting compounds of the formula IIIa are prepared by analogy processes known from the literature (for example, S. Takhashi and H. Kano, Chem. Pharm. Bull. 11 (11), 1375 et seq.).

The novel compounds of the formula I and their salts, in particular those in which R is an SR$^6$ group, possess valuable pharmacological properties.

They have a marked inhibiting action on the gastric acid secretion and, moreover, display an excellent gastro-intestinal protective action.

"Gastro-intestinal protection" is understood in this connection as the prevention and treatment of gastro-intestinal diseases, in particular gastro-intestinal inflammatory diseases and lesions (such as, for example, Ulcus ventriculi, Ulcus duodeni, gastritis, hyperacid stomach or stomach irritation due to medicaments) which may be caused, for example, by microorganisms, bacterial toxins, medicaments (for example anti-inflammatory and antirheumatic agents), chemicals (for example ethanol), gastric acid or stress situations.

Due to their excellent properties, the substituted pyrido(1,2-c)imidazo(1,2-a)benzimidazoles and their pharmacologically acceptable salts are outstandingly suitable for use in human and veterinary medicine, and they are used especially for the treatment and prophylaxis of gastro-intestinal diseases and those diseases which are caused by excessive gastric acid secretion.

The invention therefore also relates to the use of the compounds according to the invention, of the formula I, in the treatment and prophylaxis of the abovementioned diseases.

Furthermore, the invention comprises the use of the compounds according to the invention in the preparation of medicaments which are employed for the treatment and prophylaxis of the abovementioned diseases.

The invention also relates to medicaments which contain one or more compounds of the general formula I and/or their pharmacologically acceptable salts.

The medicaments are prepared by methods known per se and familiar to those skilled in the art. As medicaments, the pharmacologically active compounds according to the invention (=active ingredients) are employed either as such or, preferably, in combination with suitable pharmaceutical auxiliaries, in the form of tablets, coated tablets, capsules, suppositories, emulsions, suspensions or solutions, the active ingredient content being advantageously between 0.1 and 95%.

Those skilled in the art are, due to their specialist knowledge, familiar with suitable auxiliaries for the desired medicament formulations. In addition to solvents, gel formers, suppository bases, tablet auxiliaries and other active ingredient carriers, for example antioxidants, dispersing agents, emulsifiers, antifoaming agents, flavoring additives, preservatives, solubilizers or dyes can be used.

The active ingredients can be administered orally or parenterally, oral administration being preferred.

With oral administration, it has been proved generally advantageous in human medicine to administer the active ingredient or ingredients in a daily dose of about 0.01 to about 20, preferably 0.05 to 7, especially 0.1 to 2, mg/kg of body weight, if appropriate in the form of several, preferably 1 to 4, individual doses, for obtaining the desired result. During the treatment, similar or as a rule lower dosages (in particular in the case of intravenous administration of the active ingredients) can be applied. The particular required optimum dosage and type of administration of the active ingredients can readily be fixed by those skilled in the art, due to their specialist knowledge.

If the compounds according to the invention and/or their salts are used for the treatment of the abovementioned diseases, the pharmaceutical preparations can also contain one or more pharmacologically active ingredients from other groups of medicaments, such as antacids, for example aluminum hydroxide and magnesium aluminate; tranquillizers, such as benzodiazepines, for example diazepam; spasmolytic agents, such as, for example bietamiverine or camylofin; anticholinergic agents, such as, for example, oxyphencyclimine or phencarbamide; local anesthetics, such as, for example, tetracaine or procaine; and, if appropriate, also enzymes, vitamins or aminoacids.

For an oral administration form, the active compounds are mixed with the additives, conventional for this purpose, such as excipients, stabilizers or inert diluents, and converted by conventional methods into suitable administration forms, such as tablets, coated tablets, hard capsules, aqueous, alcoholic or oily suspensions or aqueous alcoholic or oily solutions. Examples of inert carriers which can be used are gum arabic, magnesium carbonate, potassium phosphate, lactose, glucose or starch, in particular corn starch. The preparation can be effected by either dry or wet granulation. Possible oily excipients or solvents are, for example, vegetable and animal oils, such as sunflower oil or cod-liver oil.

For subcutaneous or intravenous administration, the active compounds or their physiologically acceptable salts, if desired together with the substances conventional for this purpose, such as solubilizers, emulsifiers or other auxiliaries, are brought into solution, suspension or emulsion. Possible solvents for the novel active compounds and the corresponding physiologically acceptable salts are, for example: water, physiological salines or alcohols, for example ethanol, propanol or glycerol, and also sugar solutions such as solutions of glucose or mannitol, or a mixture of the various solvents mentioned.

The examples which follow are intended to illustrate the procedures according to the invention, without restricting the invention to the substances mentioned here as representatives.

EXAMPLES

1.
Pyrido(1,2-c)imidazo(1,2-a)benzimidazole-12-sulfenyl (a) 3 g of 2-[(2-pyridylmethyl)-sulfinyl]-benzimidazole are dissolved in 300 ml of 2N HCl and left to stand for 3 hours at room temperature. The pH is then adjusted to 7 with aqueous concentrated $NH_3$ solution, and the precipitate which has formed is filtered off. The resulting pyrido(1,2-c)imidazo(1,2-a)benzimidazole-12-sulfenyl of intense violet color can be purified by trituration with ethyl acetate or by column chromatography on silica gel with a $CHCl_3$/methanol mixture (7:3) as the solvent.

Melting point: 190° C. (decomposition).

(b) 2 g of pyrido(1,2-c)imidazo(1,2-a)benzimidazole, accessible by the methods described below, are mixed with 0.4 g of elemental sulfur and heated for 15 minutes in an oil bath to 150° C. (bath temperature). The reaction product is then taken up in $CHCl_3$/methanol (7:3) and purified by column chromatography as described under 1(a). The product is identical with that described under 1(a) in every respect.

(c) 4.1 g of pyrido(1,2-c)imidazo(1,2-a)benzimidazole are dissolved in 200 ml of tetrahydrofuran. 0.8 ml of disulfur dichloride is added at room temperature, and the mixture is stirred for a further 2 hours. After standing overnight, the product is filtered off and purified as described under 1(a). The products obtained according to 1(a)–1(c) are identical.

2.
12-Methylthio-pyrido(1,2-c)imidazo(1,2-a)benzimidazole 2.4 g of pyrido(1,2-c)imidazo(1,2-a)benzimidazole-12-sulfenyl are dissolved in 100 ml of THF, to which 10 ml of methanol have been added, and reduced at room temperature under a nitrogen atmosphere with 500 mg of $NaBH_4$ to the 12-mercapto compound which is converted, without intermediate isolation, with dimethyl sulfate (2 ml) at room temperature into the 12-methylthio compound (5 minutes reaction time). The product is isolated and purified by column chromatography on silica gel with ethyl acetate as the solvent.

Melting point: 119°–121° C.

3.
12-Acetylthio-pyrido(1,2-c)imidazo(1,2-a)benzimidazole 2.4 g of pyrido(1,2-c)imidazo(1,2-a)benzimidazole-12-sulfenyl are reduced with an $NaBH_4$ as described under 2., and then converted with 2 ml of acetic anhydride at room temperature into the 12-acetylthio compound. This is isolated and purified as described under 2.

Melting point: 117° C. (decomposition).

4. Pyrido(1,2-c)imidazo(1,2-a)benzimidazole ($a_1$) 1-(2-Picolyl)-2-chloro-benzimidazole 61.0 g of 2-chlorobenzimidazole are first added at 25° C. to a suspension of 41.9 g of sodium hydride (55–60% dispersion) in 500 ml of dimethylformamide, and 66.0 g of 2-picolyl chloride-hydrochloride are then added. The mixture is stirred for 1 hour at room temperature and for a further 2 hours at 60° C. After dilution with 1 liter of ethyl acetate, 250 ml of water are carefully added dropwise, the phases are separated, and the ethyl acetate phase is concentrated in vacuo. The remaining product melts at 75°–77° C.

($a_2$) Pyrido(1,2-c)imidazo(1,2-a)benzimidazole

The above product is heated in an excess of ethanolic hydrochloric acid (15 minutes). After cooling, the hydrochloride is filtered off with suction (melting point: 258°–260° C.) and converted with aqueous sodium hydroxide solution into the base which is isolated by filtering with suction.

Melting point: 163°–165° C.

($b_1$) N-2-Picolylidene-o-nitroaniline 27.6 g of o-nitroaniline and 21.4 g of 2-pyridine aldehyde are heated in 200 ml of toluene for 10 hours, and the water formed is collected by means of a water separator. 500 ml of diethyl ether are then added to the solution, and the crystals which precipitate are filtered off with suction.

Melting point: 108°–110° C.

($b_2$) N-2-Picolyl-o-nitroaniline

The above crystals (20 g) are dissolved in 150 ml of ethanol and reduced by means of 10 g of $NaBH_4$ at the boiling point of the alcohol within 1 hour. After addition of 20 ml of water and decomposition of the $NaBH_4$, the alcohol is evaporated in vacuo and the reduction product is filtered off.

Melting point: 86°–88° C.

($b_3$) N-2-Picolyl-o-phenylenediamine 10 g of N-2-picolyl-o-nitroaniline are hydrogenated with Raney nickel in methanol at room temperature to give the o-phenylenediamine derivative which remains as an oil, after the catalyst has been filtered off and the solvent has been evaporated in vacuo.

($b_4$) 1-(2-Pyridylmethyl)-benzimidazolin-2-one 5 g of the above o-phenylenediamine derivative are heated with 2 g of urea to 160° C. for 5 hours. After the reaction mixture has cooled, ethanol is added and the crystals which are precipitated are filtered off with suction.

Melting point: 168°–170° C.

($b_5$) Pyrido(1,2-c)imidazo(1,2-a)benzimidazole 2 g of the 1-(2-pyridylmethyl)-benzimidazolin-2-one are boiled under reflux with 10 ml of $POCl_3$ for 5 hours. The excess $POCl_3$ is then stripped off in vacuo, the residue is added to water, and the mixture is neutralized with NaOH and extracted with $CH_2Cl_2$. After drying with $Na_2SO_4$ and evaporation of the solvent, the cyclization product remains which is identical in every respect with the compound described under 4(a).

TABLE 1

| Further compounds of the formula I which have been prepared ($R^3$ to $R^5$ always = hydrogen): | | | | | |
|---|---|---|---|---|---|
| Example No. | $R^1$ | $R^2$ | R | Melting point | Preparation procedure analogous to Example |
| *5 | $CH_3$, H | H, $CH_3$ | S. | 126° C. | (1a) |

TABLE 1-continued

Further compounds of the formula I which have been prepared ($R^3$ to $R^5$ always = hydrogen):

| Example No. | $R^1$ | $R^2$ | R | Melting point | Preparation procedure analogous to Example |
|---|---|---|---|---|---|
| *6 | Bu$^t$, H | H, Bu$^t$ | S. | 248° C. | (1a) |
| 7 | H | H | SC$_2$H$_5$ | 126–127° C. | (2) |
| 8 | H | H | SCH$_2$—C$_6$H$_5$ | 163° C. (decomp.) | (2) |
| 9 | H | H | SCH$_2$—C≡CH | 156° C. (decomp.) | (2) |
| 10 | H | H | SCH$_2$—CH=CH$_2$ | 94–95° C. | (2) |
| 11 | H | H | SCO—C$_2$H$_5$ | 143–145° C. | (3) |
| 12 | H | H | SCO(CH$_2$)$_2$CH$_3$ | 138° C. | (3) |
| 13 | H | H | SCO(CH$_2$)$_5$CH$_3$ | 141° C. | (3) |
| 14 | H | H | SCO—C$_6$H$_5$ | 196–198° C. | (3) |
| 15 | H | Bu$^t$ | SCOCH$_3$ | 135° C. | (3)** |
| 16 | Bu$^t$ | H | SCOCH$_3$ | 130° C. | (3)** |
| 17 | H | H | SCOC(CH$_3$)$_3$ | 162° C. | (3) |
| 18 | OCH$_3$ | OCH$_3$ | SCOCH$_3$ | 181° C. (decomp.) | (3) |
| 19 | O—(CH$_2$)$_2$CH$_3$ | O—(CH$_2$)$_2$CH$_3$ | SCOCH$_3$ | 132° C. (decomp.) | (3) |
| 20 | H | H | SCH$_2$O(CH$_2$)$_2$OCH$_3$ | 96–97° C. | (2) |
| 21 | H | H | SCH$_2$—CH=CH$_2$ | 121–122° C. | (2) |
| 22 | H | OCH$_3$ | SCO—OC(CH$_3$)$_3$ | 149° C. | (3) |
| 23 | H | H | SCOCH(C$_2$H$_5$)$_2$ | 150–152° C. | (3) |
| 24 | H | H | S—CO—(2-furyl) | 200–201° C. | (3) |
| 25 | H | H | SCO—CH$_2$—C$_6$H$_5$ | 175–177° C. | (3) |
| 26 | H | H | SCOCH$_2$—O—C$_6$H$_4$—Cl | 162° C. | (3) |
| 27 | H | H | SCO—Cyclohexyl | 176° C. | (3) |
| 28 | H | H | SCO—CH=CH—CH$_3$ | 155° C. | (3) |
| 29 | H | H | SCOCH$_2$—OCH$_3$ | 160° C. | (3) |
| 30 | H | H | SCOCH$_2$—C$_6$H$_3$(OCH$_3$)$_2$ | 160° C.–162° C. | (3) |
| 31 | H | H | SCOCH$_2$—OC$_6$H$_5$ | 167° C. | (3) |
| 32 | H | C(CH$_3$)$_3$ | SCOCH$_3$ | 135° C. | (3) |
| 33 | C(CH$_3$)$_3$ | H | SCOCH$_3$ | 130° C. | (3) |
| 34 | H | CO—OC$_2$H$_5$ | SCOCH$_3$ | 128–129° C. | (3) |
| 35 | H | OCH$_3$ | SCO—OC(CH$_3$)$_3$ | 160° C. (decomp.) | (3) |
| *36 | H, CO—OC$_2$H$_5$ | H, CO—OC$_2$H$_5$ | S. | 154–156° C. | (1a) |
| 37 | Cl | H | S. | 197° C. (decomp.) | (1b) |

*Mixture of isomers
**After separation by column chromatography on silica gel (Grace ® 50) with ethyl acetate as eluent.
Bu$^t$ = —C(CH$_3$)$_3$

TABLE 2

Further compounds of the formula I which have been prepared ($R^1$ to $R^5$ always = hydrogen, R = S—CO—C$_6$H$_3$(R$^a$)(R$^b$))

| Example No. | $R^a$ | $R^b$ | Melting point | Preparation procedure analogous to Example |
|---|---|---|---|---|
| 38 | 4-CF$_3$ | H | 180° C. | (3) |
| 39 | 3-Cl | H | 180° C. | (3) |
| 40 | 4-C(CH$_3$)$_3$ | H | 211° C. | (3) |
| 41 | 3-OCH$_3$ | 5-OCH$_3$ | 190° C. | (3) |
| 42 | 4-CH$_3$ | H | 204° C. | (3) |
| 43 | 4-Cl | H | 174° C. | (3) |
| 44 | 3-CH$_3$ | H | 170° C. | (3) |
| 45 | 2-CH$_3$ | H | 195° C. | (3) |

TABLE 2-continued

Further compounds of the formula I which have been prepared

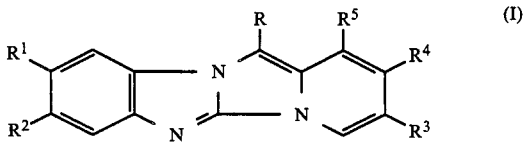

($R^1$ to $R^5$ always = hydrogen, R = S—CO—...)

| Example No. | $R^a$ | $R^b$ | Melting point | Preparation procedure analogous to Example |
|---|---|---|---|---|
| 46 | 2-Cl | H | 164° C. | (3) |
| 47 | 4-OCH$_3$ | H | 190–192° C. | (3) |
| 48 | 4-OC(CH$_3$)$_3$ | H | 205° C. | (3) |
| 49 | 4-CN | H | 184–186° C. | (3) |
| 50 | 4-(CH$_2$)$_5$CH$_3$ | H | 146° C. | (3) |
| 51 | 4-(CH$_2$)$_6$CH$_3$ | H | 182–183° C. | (3) |
| 52 | 4-Cl | 3-Cl | 157° C. | (3) |
| 53 | 4-(CH$_2$)$_4$CH$_3$ | H | 182–183° C. | (3) |
| 54 | 4-O—(CH$_2$)$_4$CH$_3$ | H | 169° C. | (3) |
| 55 | 3-OCH$_3$ | H | 184° C. | (3) |
| 56 | 2-Cl | 4-Cl | 180° C. | (3) |
| 57 | 2-CH$_3$ | 6-CH$_3$ | | (3) |
| 58 | 3-CH$_3$ | 5-CH$_3$ | | (3) |
| 59 | R = S—CO—(2,4,6-tri-CH$_3$-phenyl) | | | (3) |

60.
2-Methoxy-1,3-dimethyl-pyrido(1,2-c)imidazo(1,2-a)benzimidazole-12-sulfenyl 2 g of 1-(4-methoxy-3,5-dimethyl-2-picolyl)-benzimidazole-3-oxide are dissolved in 100 ml of CH$_2$Cl$_2$, 1 ml of trifluoroacetic anhydride is then added at room temperature, and the solution is stirred at room temperature for 1 hour. Subsequently, the reaction mixture is evaporated and the residue is washed with isopropanol.
Yield: 2 g.
Melting point: 300° C.

The 2-methoxy-1,3-dimethyl-pyrido(1,2-c)imidazo(1,2-a)benzimidazole trifluoroacetate is converted with 1N NaOh in the free base, the mixture is extracted with CH$_2$Cl$_2$ and the extract is dried over Na$_2$SO$_4$ and evaporated in a rotary evaporator. The remaining yellow oil is converted, as described in Example 1b, into the title compound by reaction with sulfur.
Yield: 1.5 g.
Melting point: 260° C. (decomposition).

EXAMPLE 61

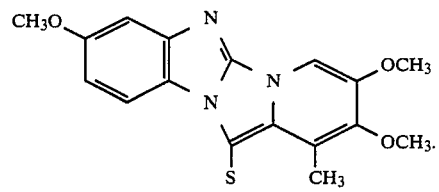

Preparation analogous to Example 60.
Melting point: 196° C.

We claim:
1. A compound of the formula I

$$\text{(I)}$$

in which $R^1$ and $R^2$ are identical or different and are hydrogen, (C$_1$ to C$_6$)-alkyl, trifluoromethyl, halogen, methoxycarbonyl, ethoxycarbonyl, (C$_1$ to C$_5$)-alkoxy or (C$_1$ to C$_4$)-alkanoyl, $R^3$, $R^4$ and $R^5$ are identical or different and are hydrogen, methyl, methoxy, ethoxy, methoxyethoxy or ethoxyethoxy and R is hydrogen or a group SR$^6$, in which R$^6$ is the lone, unpaired electron of the 12-sulfenyl radical, hydrogen, (C$_1$ to C$_6$)-alkyl which can be substituted by (C$_1$ to C$_4$)-alkoxy or mono- or poly-substituted by (C$_6$ to C$_{10}$)-aryl, or is (C$_2$ to C$_6$)-alkenyl, (C$_2$ to C$_6$)-alkynyl, (C$_1$ to C$_7$)-alkanoyl, (C$_5$ to C$_7$)-cycloalkanoyl, benzoyl which can be mono- or poly-substituted by (C$_1$ to C$_7$)-alkyl, (C$_1$ to C$_5$)-alkoxy, (C$_1$ to C$_4$)-alkoxycarbonyl, cyano, trifluoromethyl and/or halogen, or is furoyl, phenacyl, phenoxyacetyl, phenylacetyl wherein the three latter of which may be substituted as defined for benzoyl or another conventional thiol-protective group, and physiologically acceptable salts thereof.

2. A pharmaceutical composition useful to inhibit gastric acid secretions, which comprising effective amount of a compound according to claim 1 or a pharmaceutically acceptable salt thereof and a pharmaceutically acceptable carrier.

3. A method for treating gastro-intestinal diseases, caused by excessive gastric acid secretion, by administering an effective amount of a compound according to claim 1 or pharmaceutically acceptable salts thereof.

4. A method for the prophylaxis of gastro-intestinal diseases, caused by excessive gastric acid secretion, by administering an effective amount of a compound according to claim 1 or pharmaceutically acceptable salt thereof.

* * * * *